United States Patent [19]

Weber et al.

[11] Patent Number: 5,185,442
[45] Date of Patent: Feb. 9, 1993

[54] NEW DIAZEPINES SUBSTITUTED IN THE 6-POSITION, PROCESSES FOR THEIR PREPARATION AND THEIR USE AS PHARMACEUTICAL COMPOSITIONS

[75] Inventors: Karl-Heinz Weber; Werner Stransky, both of Gau-Algesheim; Ulrike Kuefner-Muehl, Ingelheim; Hubert Heuer, Schwabenheim; Franz Birke, Ingelheim am Rhein; Wolf-Dietrich Bechtel, Appenheim, all of Fed. Rep. of Germany

[73] Assignee: Boehringer Ingelheim KG, Ingelheim am Rhein, Fed. Rep. of Germany

[21] Appl. No.: 821,514

[22] Filed: Jan. 15, 1992

[30] Foreign Application Priority Data

Jan. 16, 1991 [DE] Fed. Rep. of Germany ....... 4101146

[51] Int. Cl.$^5$ .................... C07D 513/14; A61K 31/55
[52] U.S. Cl. .................................................. 540/555
[58] Field of Search ......................................... 540/555

[56] References Cited

PUBLICATIONS

Chemical Abstracts vol. 112 (1990) abstracting EPO 328,924 Aug. 23, 1989.
Chemical Abstracts vol. 113 (1990) abstracting German Offen. D.E. 3,936,828, May 10, 1990.
Chemical Abstracts vol. 115 (1991) abstracting EPO 407,955 Jan. 16, 1991.

*Primary Examiner*—Robert T. Bond
*Attorney, Agent, or Firm*—David E. Frankhouser; Daniel Reitenbach; Mary-Ellen M. Timbers

[57] ABSTRACT

The invention relates to new diazephines of the formula

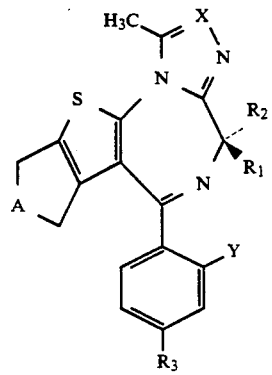

wherein $R^1$, $R^2$ and $R^3$ are as defined herein, processes for preparing them and their use as pharmaceutical compositions useful for treating PAF-induced disease.

3 Claims, No Drawings

NEW DIAZEPINES SUBSTITUTED IN THE 6-POSITION, PROCESSES FOR THEIR PREPARATION AND THEIR USE AS PHARMACEUTICAL COMPOSITIONS

The invention relates to new diazepines, processes for their preparation and their use as pharmaceutical compositions having a PAF-antagonistic effect.

The new diazepines correspond to general formula I

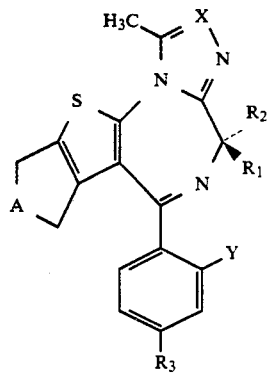

wherein
A represents —CH$_2$— or —CH$_2$—CH$_2$—
X represents nitrogen, C—H or C—CH$_3$;
Y represents hydrogen or halogen;
R$_1$ represents hydrogen or CH$_3$;
R$_2$ represents hydrogen or CH$_3$;
R$_3$ represents

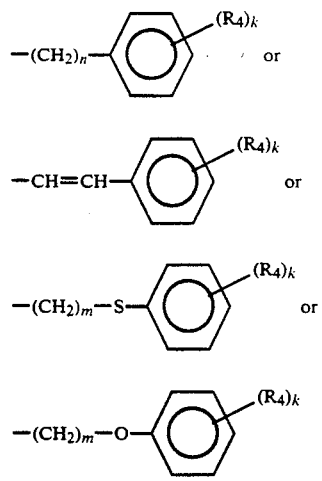

wherein
n = 1, 2, 3 or 4—preferably 2—,
m = 1, 2 or 3—preferably 1—,
R$_4$ represents hydrogen, halogen, CF$_3$, C$_{1-4}$-alkyl, cycloalkyl, methoxy, trifluoromethoxy, CN,
k = 1, 2 or 3 whilst if k is > 1 R$_4$ may be identical or different,
with the proviso that if Y represents hydrogen, R$_1$ and R$_2$ cannot both together represent hydrogen;
optionally in the form of their racemates, enanthiomers, diastereomers and mixtures thereof.

Diazepines of general formula Ia are preferred,

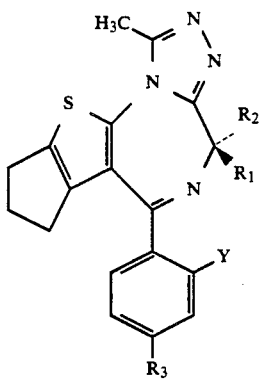

wherein
Y represents hydrogen, bromine or chlorine
R$_1$ and R$_2$ are defined as hereinbefore;
R$_3$ represents

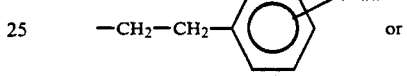

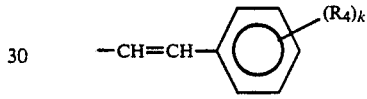

(in the trans configuration) or

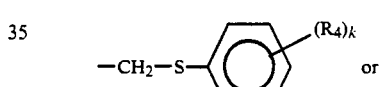

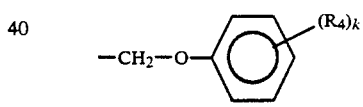

R$_4$ represents hydrogen, chlorine, bromine, trifluoromethyl, methyl, isobutyl or methoxy, whilst R$_4$ is preferably in the 4-position of the phenyl ring, optionally in the form of their racemates, enantiomers, diastereomers and mixtures thereof.

The compounds according to the invention may have a center of asymmetry in the diazepine ring if R$_1$ and R$_2$ are different.

The S-configured diazepines of general formulae I and Ia, wherein R$_1$=hydrogen, R$_2$=methyl and Y=-halogen, preferably chlorine, are particularly preferred.

Within the scope of the definitions, C$_{1-4}$-alkyl represents a branched or unbranched C$_{1-4}$-alkyl group such as methyl, ethyl, propyl, isopropyl, n-butyl, isobutyl, sec.-butyl and tert.-butyl. The definition halogen denotes F, Cl, Br or iodine.

The mixtures of optically isomeric compounds which may be produced during synthesis may optionally be resolved into the individual optical isomers by the formation of diastereomers and subsequent separation using methods known per se, e.g. by crystallisation, chromatography or enzymatic separation.

As is known, PAF (platelet activating factor) is the phospholipid acetyl-glyceryl-ether-phosphoryl-choline (AGEPC), which is known as a potent lipid mediator released by proinflammatory animal and human cells. Such cells chiefly include basophilic and neutrophilic granulocytes, macrophages (from blood and tissue) and platelets, which participate in inflammation reactions.

In pharmacological experiments, PAF results in bronchoconstriction, a reduction in blood pressure, inducement of platelet aggregation and a proinflammatory action.

These experimentally detectable actions of PAF directly or indirectly indicate possible functions of this mediator in anaphylaxis, in the pathophysiology of bronchial asthma and generally in inflammation.

PAF antagonists are required on the one hand to clarify further pathophysiological functions of this mediator in animals and humans and on the other hand to treat pathological conditions and diseases in which PAF participates. Examples of the indications of a PAF antagonist are inflammation processes of the tracheobronchial tree (acute and chronic bronchitis, bronchial asthma) or of the kidney (glomerulonephritis), of the joints (rheumatic diseases), anaphylactic states, allergies and inflammations in the region of the mucosa and skin (e.g. psoriasis) and shock states caused by sepsis, endotoxins or burns. Other important indications for a PAF antagonist are lesions and inflammations in the region of the gastric and intestinal mucosa, such as e.g. gastritis, peptic ulcers in general, but in particular gastric ulcers and duodenal ulcers; and for treating thrombosis.

The compounds according to the invention are furthermore suitable for the treatment of the following diagnoses: Obstructive pulmonary diseases, such as e.g. bronchial hyperreactivity, inflammatory diseases of the pulmonary tract, such as e.g. chronic bronchitis; allergic rhinitis; cardiovascular diseases, such as e.g. polytrauma, anaphylaxis, arteriosclerosis, inflammatory intestinal diseases, EPH gestosis (oedema- proteinuria- hypertension), diseases of the extracorporal circulation, ischaemic diseases, inflammatory and immunological diseases, immunomodulation for transplants of foreign tissues, immunomodulation for leukaemia, the spread of metastases, e.g. with bronchial neoplasia, and diseases of the CNS, such as e.g. migraine, agoraphobia (panic disorder), and the compounds according to the invention furthermore prove to be cyto- and organoprotective, e.g. for neuroprotection, e.g. in cases of cirrhosis of the liver, DIC (disseminated intravasal coagulation); side effects of medicament therapy, e.g. anaphylactoid circulatory reactions, contrast medium incidents, side effects of tumour therapy; haemolytic uremic syndrome; incompatibilities with blood transfusions; fulminant liver failure ($CCl_4$ intoxication); Amanita phalloides intoxication (death-head intoxication); symptoms of parasitic diseases (e.g. worm diseases); autoimmune diseases.

The following indications are furthermore of interest: Immune function in cases of Aids, diabetes, juvenile diabetes, diabetic retinopathy, polytraumatic shock, haemorrhagic shock, CNS: ischaemia, multiple sclerosis, migraine, colitis ulcerosa, Crohn's disease, psoriasis, high pulmonary pressure and chronic ischaemic cardiac insufficiency. PAF antagonists of the general formula Ia are suitable for the treatment of pathological changes in blood gases, such as, for example, respiratory acidosis, metabolic alkalosis. PAF antagonists can be used in combination with anticholinergics to improve the blood gas values in cases of phosphoric acid ester intoxication. It is known that PAF antagonists by themselves—or in combination with immunosuppressive compounds (e.g. cyclosporins)—can be used for the treatment of autoimmune diseases and in transplant cases.

The use of PAF antagonists in combination with antihistamines is furthermore proposed. With regard to the definition of antihistamines, the content of European Patent Application 345 731 is referred to. It is furthermore known that PAF antagonists in combination with $\beta_2$-mimetics can be used for the treatment of bronchial asthma. Combination of PAF antagonists with TNF is also advantageous. PAF-associated interaction with tissue hormone (autocoid hormones), lymphokines and other mediators.

The new hetrazepines are very potent PAF antagonists and are superior to other known diazepinoid PAF antagonists in the following criteria:
  there is total dissociation between the PAF antagonism and the effects mediated to the benzodiazepine receptor;
  superior binding affinity with the PAF receptor on washed human platelets, and they exhibit a greater inhibition of PAF-induced platelet aggregation;
  they moreover inhibit, in a superior manner, bronchoconstriction induced by PAF (30 ng/kg×min) after oral and parenteral administration to guinea pigs, in combination with a very long action time (more than 15 h after oral administration to guinea pigs).

The inhibition of PAF-induced platelet aggregation can be determined using the following method:

200 ml samples of blood were taken from a nonobstructed vein, with the aid of a plastic syringe containing 3.8% sodium citrate solution, from healthy male and female donors aged from 18 to 35 years who had not taken any medicaments (aspirin or other non-steroid anti-inflammatories) for several days before the blood withdrawal. The ratio of sodium citrate solution:blood was 1:9. The citrated blood was centrifuged in plastic tubes at $150 \times g$ (=1,200 rpm) at room temperature for 20 min (Heraeus Christ bench centrifuge 124).

The platelet aggregation was measured in vitro by the method of Born and Cross (1963), an aggregation inducer (PAF) being added to the TRP, while stirring constantly. For the measurement, 0.8 ml TRP and 0.2 ml modified Tyrode's solution (see below) were introduced into 1 ml plastic cells, each of which contained a small metal pin (stirrer, 1,000 rpm). The test substance was added in a volume of 10 $\mu$l 2 to 3 min before inducing the aggregation. Either DMSO and water or a dilute HCl solution was used as the solvent. The control batches contained the corresponding volume of these solvents. After recording the initial absorption (2–3 min), aggregation was induced. PAF ($5 \times 10^{-8}$ M; Bachem Feinchemikalien) was introduced into the cell in a volume of 10 $\mu$l.

The modified Tyrode's solution had the following composition: 136.9 mM NaCl; 2.68 mM KCl; 0.5 mM $MgCl_2$; 1.8 mM $CaCl_2$; 0.42 mM $NaH_2PO_4$; 5.55 mM glucose and 11.9 mM $NaHCO_3$.

To evaluate substance effects, the maximum of the first aggregation wave was used. The maximum absorption induced by the aggregation inducer (=maximum aggregation=100%) was simultaneously run in a parallel batch (in the 2nd channel of the aggregometer) to each test batch and used as the 100% value. The aggregation value achieved under the action of the test substance was quoted as % of the control value (batch). Concentration/effect curves with a random sample size of in each case n=4 were plotted with the aid of this method and IC$_{50}$ values (concentration at 50% aggregation inhibition) were calculated.

The compounds according to the invention may be prepared by methods analogous to those of the prior art.

Synthesis is carried out according to the following reactions, in accordance with European Patent 194 416 and European Patent Applications 230 942 and 254 245.

Starting from the correspondingly substituted diazepinethionene of general formula

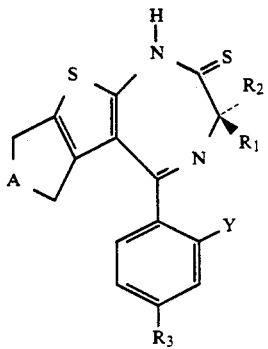

wherein A, R$_1$, R$_2$, R$_3$ and R$_4$ are defined as hereinbefore, the compounds of general formula I or Ia according to the invention are obtained A) if X represents nitrogen
  a) by reacting with an acid hydrazide of general formula

CH$_3$—CONHNH$_2$     (III), b) or by converting with hydrazine into a compound of the general formula and subsequently reacting with an acid halide of general formula CH$_3$—CO—Hal or with an orthoester of general formula CH$_3$—C(OR')$_3$ wherein R' represents a lower alkyl group, or B) if X represents C—H
  a) reacting with an aminoalkyne of general formula

R$_1$'—C≡C—CH$_2$—NH$_2$ wherein R'$_1$ represents hydrogen or a lower methyl group or
  b) reacting with an α-aminoaldehyde-alkylacetal or α-aminoketone-alkylketal of general formula

H$_2$NCH$_2$—CCH$_3$(OR')$_2$ wherein R' represents a lower alkyl group, and subsequently, if desired, cleaving the resulting compounds into their optically active compounds using methods of separation known per se.

The reaction of the thione II with an acid hydrazide III according to process a) is carried out in an inert organic solvent, e.g. dioxane, dimethyl-formamide, tetrahydrofuran or a suitable hydrocarbon, e.g. benzene or toluene, at temperatures between ambient temperature and the boiling point of the reaction mixture. The end products are isolated by known methods, e.g. by crystallisation.

The reaction of the thione II with hydrazine according to process b) is carried out in inert organic solvents such as tetrahydrofuran, dioxane, halogenated hydrocarbons such as methylene chloride, or suitable hydrocarbons, at temperatures between ambient temperature and the boiling point of the reaction mixture.

The hydrazine-1,4-diazepines thus obtained can be isolated by conventional methods or further processed directly.

Further reaction with an acid halide or orthoester takes place in an inert organic solvent such as halogenated hydrocarbons or cyclic or aliphatic esters but may also be carried out directly in the substance. The end product Ia is isolated by known methods, e.g. by crystallisation. Further details of the method of preparation can be found in the detailed reaction scheme and in the Examples.

Compounds of general formula

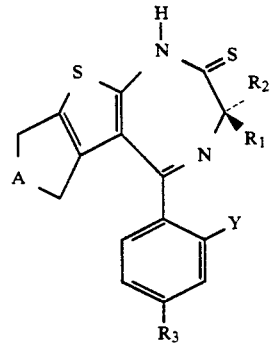

wherein A, R$_1$, R$_2$, R$_3$ and R$_4$ are defined as hereinbefore are useful starting products for the preparation of hetrazepines with a PAF-antagonistic effect and are claimed as such.

The basic structure of the compounds according to the invention is built up in a manner known per se [EP-OS 254 245 and EP-PS 194 416] and is diagrammatically shown in the following reaction scheme; however, the process is not restricted to the groups shown.

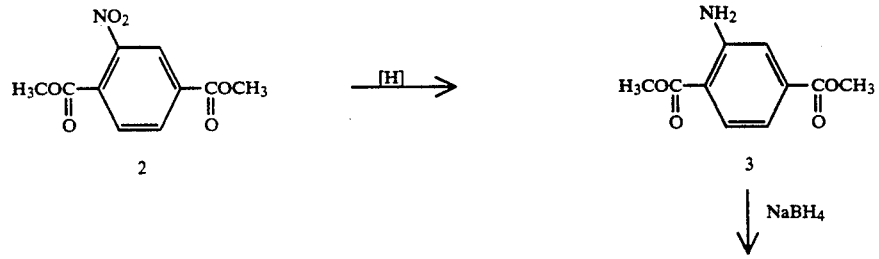

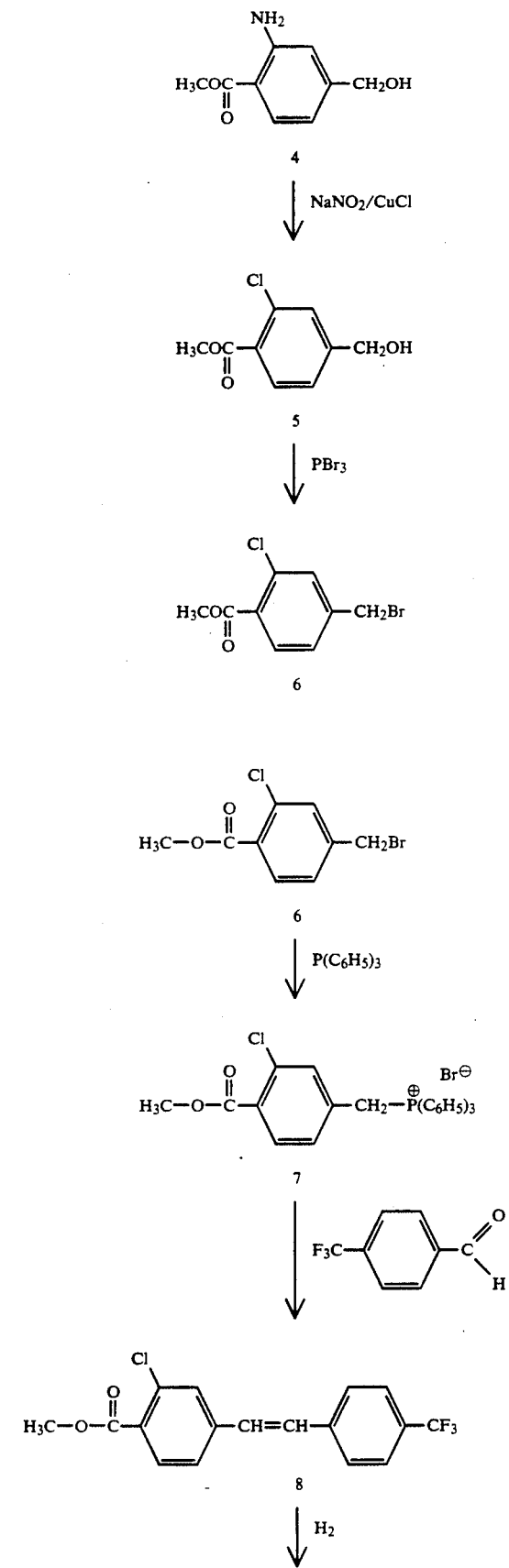

-continued
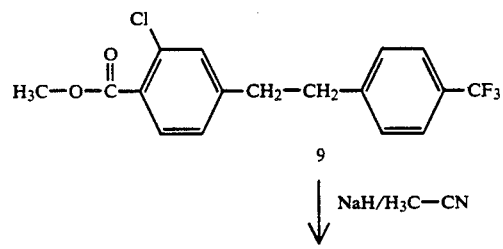
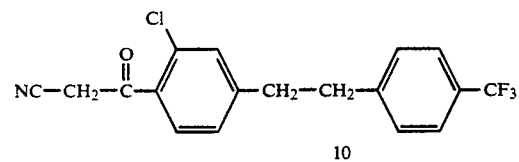
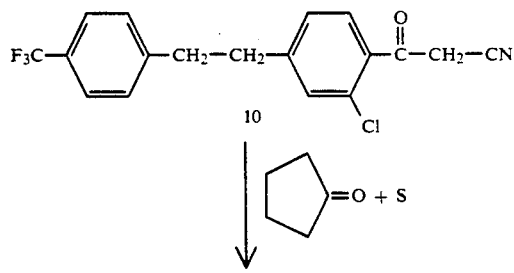
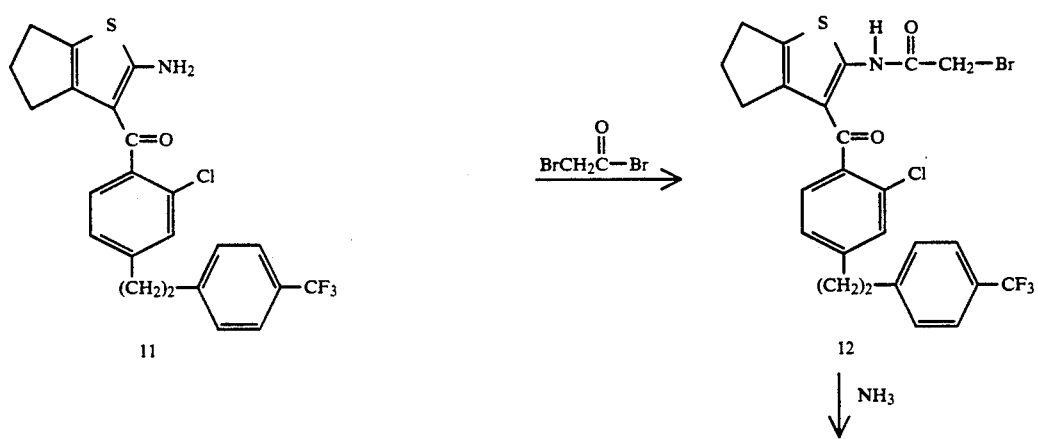

5,185,442
-continued
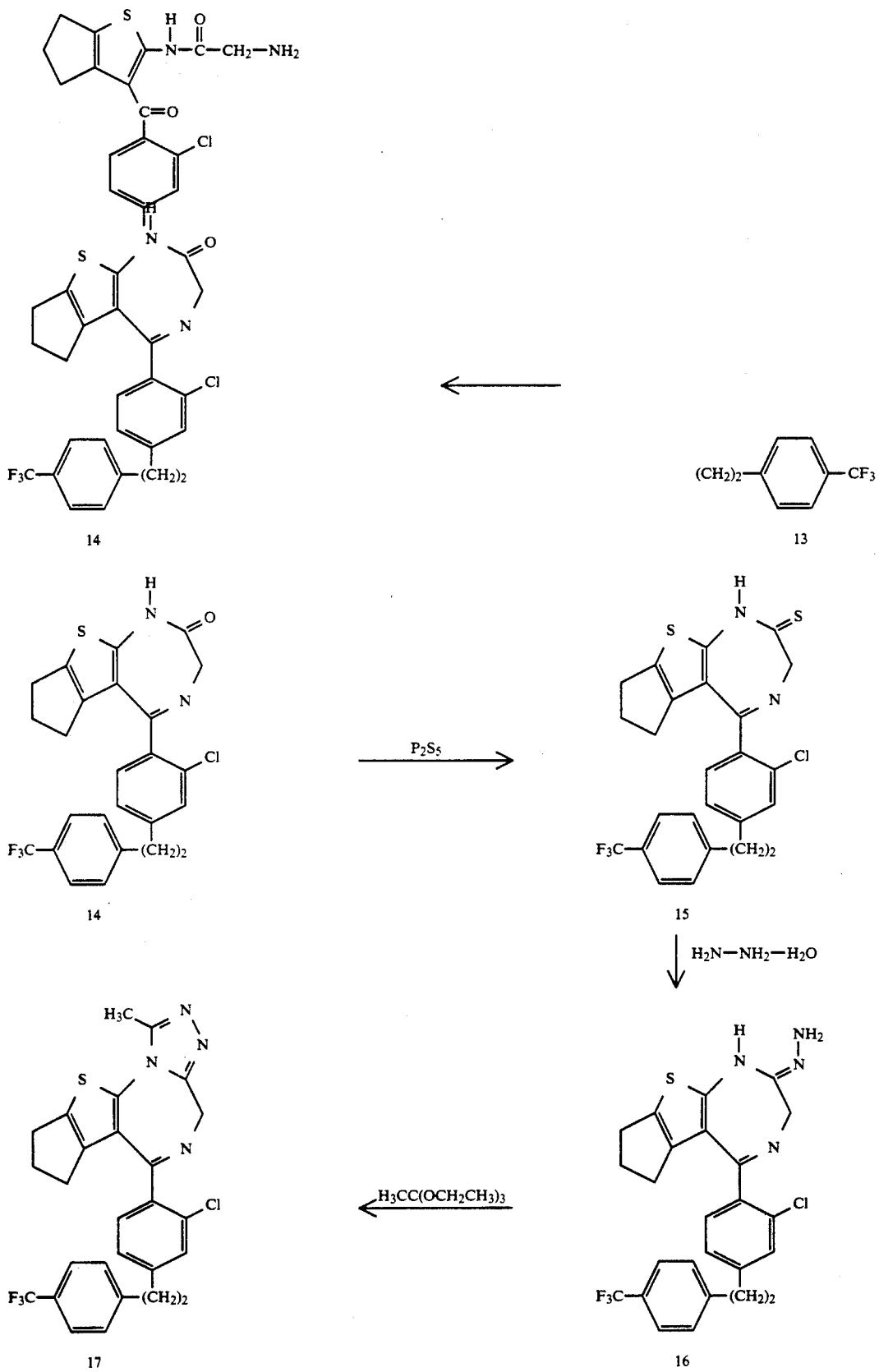

EXAMPLE 1

6-(2-Chloro-4-[2-(4-trifluoromethylphenyl)ethyl-phenyl]-8,9-dihydro-1-methyl-4H,7H-cyclopenta[4,5]-thieno[3,2-f]-[1,2,4]triazolo[4,3-a][1,4]-diazepine

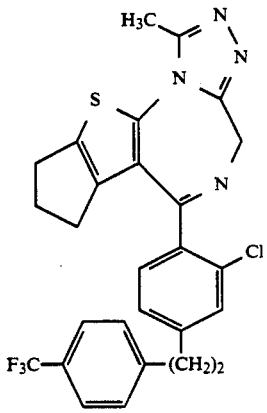

a) Dimethyl 2-aminoterephthalate 23.9 g (0.1 mol) of dimethyl 2-nitroterephthalate are hydrogenated in a mixture of 100 ml of methanol and 200 ml of tetrahydrofuran with palladium/charcoal at 5 bar and 20° C. After the catalyst has been removed by suction filtering the solvent is evaporated off and the residue is recrystallised from methanol. Yield 18-19 g, yellowish crystals m.p. 130-131° C.

b) Methyl 2-amino-4-hydroxymethyl-benzoate 10.5 g (0.05 mol) of dimethyl 2-aminoterephthalate are suspended in 150 ml of tert.butanol, 5.7 g (0.15 mol) of sodium borohydride are added and the mixture is heated to 85°. After stirring for 1 hour at this temperature, 15 ml of methanol are gradually added dropwise with simultaneous refluxing. Then the reaction mixture is boiled for a further hour, with stirring, then cooled and extracted three times with 50 ml of saturated saline solution. The butanol is distilled off in vacuo and the residue is recrystallised from ethyl acetate. 6-7 g of the desired amino alcohol are obtained in the form of white crystals, m.p. 102°-103° C., which contain only a little of the isomeric carbinol.

$^1$H-NMR (CD$_3$OD):δ=7.72(1H,d,J=7.0Hz,); 6.73(1H,d,J=2Hz, H$_m$); 6.52(1H,dd,J=7.0, 2.0Hz,); 4.50 (2H,s,CH$_2$—O); 3.80 (3H,s,OCH$_3$); NH$_2$, OH in the solvent blind peak.

c) Methyl 2-chloro-4-hydroxymethyl-benzoate 18.1 g (0.1 mol) of the above amino compound are dissolved in 50 ml of water and 50 ml of conc. hydrochloric acid. At 2°-5° C., a solution of 6.9 sodium nitrite in 50 ml of water are gradually added with stirring and the resulting mixture is stirred for a further 5 minutes. The diazonium salt solution obtained is then gradually added dropwise at 5° to 14 g of copper-I-chloride in 100 ml of concentrated hydrochloric acid. The reaction mixture is then heated to 85° for 15 minutes. It is cooled, extracted twice with 100 ml of methylene chloride, the organic phase is dried and the solvent is distilled off. 16-17 g of colourless carbinol are left.

$^1$H-NMR(CD$_3$OD):δ=7.77(1H,d,J=7.0Hz); 7.47(1H,d,J=2.0Hz, Hm); 7.32(1H,dd,J=7.0,2.0Hz,); 4.62(2H,s,CH$_2$—O); 3.89(3H,s,OCH$_3$); OH in the solvent blind peak.

d) 2-Chloro-1-carbomethoxy-triphenvlphosphonium-methyl bromide 34 g (0.17 mol) of the above carbinol are dissolved in 400 ml of methylene chloride and at 5°-8° C., 10 ml of phosphorus tribromide are slowly added, with stirring. The mixture is stirred for 1 hour at ambient temperature, the pH is shifted to 8 by the addition of dilute ammonia, the methylene chloride phase is separated off and, after drying and evaporation, 26-28 g of residue are obtained, m.p. 39°-40° C. This is taken up in 200 ml of benzene, 26.5 g of triphenylphosphine are added and the resulting mixture is refluxed for 6 hours. After cooling, the crystals are suction filtered and washed with a little benzene. After drying, 50-55 g of pure triphenylphosphonium salt are obtained, m.p. 226°-228° C.

e) Methyl 2-chloro-4-trifluoromethylphenylethylene benzoate 4 g of sodium hydride dispersion (50%) are added to 100 ml of absolute dimethylsulphoxide and stirred for 45 minutes at 80° C. under nitrogen. The mixture is cooled to 10° C. and 53 g of the above phosphonium salt are added in batches, with further cooling. After about 10 minutes, a solution is formed to which 17.4 g of 4-trifluorobenzaldehyde are added at ambient temperature. The mixture is stirred for 2 hours at ambient temperature, diluted with 3,000 ml of ethyl acetate and the mixture is extracted twice with 100 ml of water. 26 g of the expected cis-trans isomer mixture is obtained from the organic phase, and this mixture can be separated by treatment with diisopropylether. Yield: 8 g of a crystalline fraction of the trans compound, m.p. 90°-92° C., and 20 g of the oily cis compound.

d) Methyl 2-chloro-4-trifluoromethylethyl benzoate 18 g of the above olefin are hydrogenated in 300 ml of tetrahydrofuran with the aid of Raney nickel under 5 bar and at 20° C. After separation of the catalyst, evaporation of the solvent and chromatography of the residue over SiO$_2$ (eluant toluene) 17 g of the desired ester are obtained, m.p. 58°-59° C.

Calculated: C,59.5; H,4.12; Cl,10.34, Found: C,59.90; H,4.45; Cl,9.98.

e) 2-Chloro-4-trifluoromethylphenylethylphenyl-carbonylacetonitrile

A mixture of 17 g (0.25 mol) of the above ester, 240 ml of toluene, 4 ml of acetonitrile and 2.4 g of sodium hydride dispersion (50%) is refluxed for 6 hours with vigorous stirring. After cooling, 250 ml of ethyl acetate are added and the mixture is slowly acidified with 2 n hydrochloric acid. The aqueous phase is separated off, the organic phase is washed again with water and dried. After evaporation and chromatography over SiO$_2$ (eluant toluene) 12 g of the desired cyanoketone are obtained together with 5 g of starting material.

f) 2-Amino-3-(2-chloro-4-(ethyl-4-(trifluoromethylphenyl))benzoyl-cyclopentano4,5]thiophene 12 g of the above cyanoketone, 30 ml of ethanol, 3 g of cyclopentanone, 1.1 g of sulphur and 2.8 ml of triethylamine are refluxed for 6 hours. The reaction mixture is evaporated down in vacuo, the residue is diluted with methylene chloride and washed with water, then dried, the solvent is again distilled off and the residue is chromatographed over SiO$_2$ (eluant methylene chloride/methanol (99:1)). 6–8 g of the desired aminothiophene are obtained. Analogously to the process described in our Application EP 254 245, the corresponding 1,4-diazepinone is synthesised, starting from the above aminothiophene, by bromoacylation, followed by treatment with gaseous ammonia in ethyl acetate and subsequent treatment of the amino compound with SiO$_2$ in boiling toluene using the water separator.

From this 1,4-diazepinone, the diazepinethione is obtained by treating with phosphorus pentasulphide and the corresponding hydrazino compound is obtained therefrom, m.p. 198°–200° C. The latter is converted, as described in European Patent Application 254 245, with triethyl orthoacetate into the desired title compound, which melts at 200°–201° C.

$^1$H-NMR(CDCl$_3$):δ = 7.53–7.02(7H,m,aryl-H); 4.86(2H,s,broad, CH$_2$-7 ring); 2.96(6H,m,aryl-CH$_2$CH$_2$; CH$_2$-9; 5-ring); 2 70(3H,s,CH$_3$-triazole); 2.38–1.83(4H,m,CH$_2$8/7; 5-ring).

EXAMPLE 2

6-[4-[2-(4-Trifluoromethylohenyl)ethylphenyl]-8,9-dihydro-1,4,4-trimethyl-4H,7H-cyclopenta[4,5]thieno-[3,2-f][1,2,4]triazolo[4,3-a][1,4]diazepine

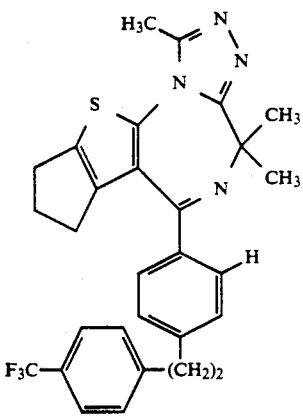

a) 11.5 g (70 mmol) of methyl 4-hydroxymethylbenzoate are added to 120 ml of dichloromethane and 47.3 ml of phosphorus tribromide are added thereto. The mixture is stirred for one hour at ambient temperature and a semi-concentrated solution of ammonia in water is carefully added, whilst cooling with ice, until a pH of 8 to 9 is achieved. The organic phase is separated off and dried and the solvent is distilled off. 13.4 g (84% of theory) of the methyl 4-bromomethylbenzoate are obtained (analogously to Compound 6).

b) Phosphonium salt:

13.3 g (58 mmol) of methyl bromomethylbenzoate are refluxed for 6 hours with 15.1 g of triphenylphosphine in 130 ml of benzene. The crystals obtained during the reaction are suction filtered and dried. 27.4 g (96% of theory) of phosphonium bromide of the type 7 are obtained in the form of crystals, m.p. 258°–260° C.

c) Wittig olefination

In a nitrogen atmosphere, 8.7 g of 55% sodium hydride dispersion are added to 100 ml of absolute dimethylsulphoxide and stirred at 80° C. for 45 minutes. After cooling to ambient temperature, a suspension of 98 g (0.2 mol) of phosphonium salt 4 is added dropwise and the reaction mixture is stirred for a further 10 minutes. Then 34.8 g of trifluoromethylbenzaldehyde are added dropwise and the mixture is stirred for 2 hours at ambient temperature. The mixture is then diluted with 400 ml of ethyl acetate and washed twice with water. The organic phase is dried and the residue is chromatographed (SiO$_2$ column, eluant: dichloromethane). The main fraction is evaporated down in vacuo and the residue is recrystallised from isopropylether. 37.5 g (61% of theory) of stilbene of the type 8 are obtained in the form of crystals, m.p. 157°–158° C.

d) 37 g (0.12 mol) of the olefin thus obtained are hydrogenated in 600 ml of tetrahydrofuran with Raney nickel as catalyst at 20° C. under 5 bar. Once the catalyst has been removed by suction filtering, the tetrahydrofuran is evaporated off and 33.5 g of the corresponding diphenylethane derivative of type 9 are obtained in the form of white crystals (90% of theory), m.p. 88°–90° C.

e) 33 g (0.1 mol) of the ester hydrogenated in this way are dissolved in 100 ml of toluene. 4.8 g of a 55% sodium hydride dispersion and then 6.9 ml of acetonitrile are added and the reaction mixture is refluxed for 6 hours. After cooling, the mixture is acidified with dilute hydrochloric acid to pH 5 to 6. The suspension is extracted 3 times with dichloromethane, the organic extracts are dried and concentrated by evaporation in vacuo. The residue is chromatographed over an SiO$_2$ column using dichloromethane as eluant. The main fraction is evaporated down, whereupon the residue crystallises. Yield: 15.5 g (46% of theory); m.p.: 105° C.

f) 155 g (488 mmol) of type 10 cyanoketone, 46 g of cyclopentanone and 17.4 g of sulphur are suspended or dissolved in 270 ml of dimethylformamide. Then 38 ml of triethylamine are added and the mixture is stirred for a further 3 hours at 60° C. After cooling, the reaction mixture is diluted with ethyl acetate and the organic phase is washed twice with water. After evaporation of the solvents in vacuo the residue is added to an SiO$_2$ column and the desired product is eluted with dichloromethane. The residue can be crystallised by the addition of isopropylether/petroleum ether. 64 g of aminoketone of the type 11 are obtained (32% of theory) with a melting point of 140°–150° C.

g) 20.7 g (0.05 mol) of the 2-amino-3-[[2-(4-trifluoromethylphenyl)ethyl]phenyl]benzoylcyclopentano[4,5]thiophene thus obtained are dissolved or suspended in 200 ml of dichloromethane and 5.3 ml of pyridine are added. At ambient temperature, 6.8 ml (0.055 mol) of 2-bromo-isobutyric acid bromide are added dropwise, with stirring, and the mixture is stirred for a further hour. The reaction mixture is evaporated down to one third of its volume in vacuo and then poured onto an SiO$_2$ column. It is eluted with dichloromethane and, after evaporation of the eluate, 22.5 g of the bromo-compound of type 12 are obtained from the residue, by recrystallisation from a mixture of ether and petroleum ether, in the form of bright yellow crystals, m.p. 132°–135° C.

h) 11.3 g of the type 12 bromo-compound are mixed with 14 ml of ethyl acetate, 10 ml of dichloroethane and 1 g of liquid ammonia and shaken for 1 hour at 100° C. under 8 bar. The cooled reaction mixture is washed with water. 10 g of the corresponding amino compound of type 13 are obtained from the organic phase, after drying and evaporation in the form of a thinly viscous oil.

i), The amino compound thus obtained is refluxed for 2 hours together with 50 g of SiO$_2$ and 200 ml of toluene, using a water separator. After cooling, the silica gel is removed by suction filtering and extraction is carried out three times with 100 ml of ethanol. The residue of the combined and evaporated eluates is chromatographed on a SiO$_2$ column (dichloromethane/methanol 99:1). 4 g of the desired diazepinone of type 14 are obtained. From this, in accordance with EP 254 245, using phosphorus pentasulphide in pyridine at 60° C., the corresponding thione of type 15 is obtained as a solid red product which is converted with hydrazine hydrate into the corresponding hydrazide of type 16. 1.75 g of this hydrazide are taken up in 10 ml of ethanol and 1.5 ml of triethylorthoacetate and refluxed for 1 hour. The reaction mixture is evaporated down in vacuo, chromatographed on a column filled with SiO$_2$ (eluant: dichloro-methane/methanol 97 : 3) and the title compound is obtained in the form of crystals, m.p. 187°–189° C., from the main fraction after the addition of diethylether.

$^1$H-NMR(CDCl$_3$):δ = 7.52–7.03(8H,m,aryl-H); 2.95(6H,m,aryl-CH$_2$CH$_2$; CH$_2$-9, 5-ring); 2.69(3H,s,CH$_3$-triazole); 2.37–1.95(4H,m,CH$_2$CH$_2$8/7); 1.19(6H,s,broad, C(CH$_3$)$_2$

EXAMPLE 3

6-(4-Ethyl(4-trifluoromethylphenyl)-8,9-dihydro-1-methyl-R,S-4-methyl-4H,7H-cyclopenta[4,5]thieno -[3,2-f][1,2,4]triazolo[4,3-a][1,4]diazepine Starting from 2-amino-3-(4-ethyltrifluoromethylphenyl)-benzoylcyclopentano[4,5]thiophene (cf. EP 254 245) the corresponding propionyl derivative was obtained with 2-bromopropionic acid bromide analogously to the above method and this propionyl derivative together with ammonia in ethyl acetate/dichloroethane and subsequent treatment with SiO$_2$ in boiling toluene, yields the corresponding racemic diazepinone. The thione is obtained therefrom, using phosphorus pentasulphide, in the form of yellow crystals, m.p. 220° C. The hydrazino compound which can be obtained from this melts at 223° C. and, with triethylorthoacetate, yields the racemic title compound, m.p. 162°–163° C.

$^1$H-NMR(CDCl$_3$):δ = 7.51–7.03(8H,m,aryl-H); 4.20(1H,qu,J = 6.0Hz, CH—CH$_3$); 2.95(6H,m,aryl-CH$_2$CH$_2$; CH$_2$-9, 5-ring); 2.62(3H,s,CH$_3$-triazole); 2.43–2.02(4H,m,CH$_2$8/7 5-ring); 2.11(3H,d,J = 6Hz, CH—CH$_3$).

Separation of Enantiomers Using a Chiral Column 1 g of the racemate obtained above is dissolved in 10 ml of a 60:40 mixture of oyolohexane and isopropanol in an ultrasonio bath and added to a Chiraspher column made by E. Merck of Darmstadt (particle size 5 μm). Elution is carried out with cyclohexane/isopropanol 60:40 at a rate of 2 ml per minute. This is carried out by a recycling operation. After the two enantiomers have been totally separated, the solutions are worked up preparatively.

The eutomer (S-configuration) is obtained as a second fraction, after distillation of the eluant, in the form of crystals, m.p. 164°–165° and with an optical rotation [α]$_D$ = +49.9 (methanol) and an optical purity of more than 99%.

The first fraction contains the distomeric compound (R-configuration) with an optical rotation of [α]$_D$ –48° (methanol).

The following compounds, for example, may be prepared analogously to the general synthetic scheme and the detailed Examples:

6-{2-chloro-4-[2-(4-trifluoromethylphenyl)ethyl]-phenyl}-8,9-dihydro-1,4-dimethyl-4H,7H-cyclopenta[4,5]thieno -3,2-f][1,2,4]triazolo[4,3-a][1,4]diazepine 6-{2-chloro-4-[2-(4-trifluoromethylphenyl)ethyl]-phenyl}-8,9-dihydro-1-methyl-4H,7H-cyclopenta[4,5]thieno[3,2-f]-1,2,4]triazolo[4,3-a][1,4]diazepine 6-{4-[2-(4-trifluoromethylphenyl)ethyl]phenyl}-8,9-dihydro-1,4-dimethyl-4H,7H-cyclopenta[4,5]thieno -3,2-f][1,2,4]triazolo[4,3-a][1,4]diazepine 6-[2-chloro-4-(2-phenylethyl)phenyl]-8,9-dihydro-1,4-dimethyl -4H,7H-cyclopenta[4,5]thieno[3,2-f][1,2,4]-triazolo[4,3-a][1,4]diazepine 6-[2-chloro-4-(2-phenylethyl)phenyl]-8,9-dihydro-1-methyl-4H,7H -cyclopenta[4,5]thieno[3,2-f][1,2,4]-triazolo[4,3-a][1,4]diazepine 6-[4-(2-phenylethyl)phenyl]-8,9-dihydro-1,4-dimethyl-4H,7H -cyclopenta[4,5]thieno[3,2-f][1,2,4]triazolo -[4]triazolo-[4,3-a][1,4]diazepine 6-{2-chloro-4-[2-(4-chlorophenyl)ethyl]phenyl}-8,9-dihydro-1,4-dimethyl-4H,7H-cyclopenta[4,5]thieno -[3,2-f][1,2,4]triazolo[4,3-a][1,4]diazepine 6-{2-chloro-4-[2-(4-chlorophenyl)ethyl]phenyl}-8,9-dihydro-1-methyl-4H,7H-cyclopenta[4,5]thieno[3,2-f]-[1,2,4]triazolo[4,3-a][1,4]diazepine 6-{4-[2-(4-chlorophenyl)ethyl]phenyl}-8,9-dihydro-1,4-dimethyl -4H,7H-cyclopenta[4,5]thieno[3,2-f][1,2,4]-triazolo[4,3-a][1,4]diazepine 6-{2-chloro-4-[(4-trifluoromethylphenyl)thiomethyl]-phenyl}-8,9-dihydro-1,4-dimethyl-4H,7H-cyclopenta -[4,5]thieno[3,2-f][1,2,4]triazolo[4,3-a][1,4]diazepine 6-{2-chloro-4-[(4-trifluoromethylphenyl)thiomethyl]-phenyl}-8,9-dihydro-1-methyl-4H,7H-cyclopenta[4,5]-thieno[3,2-f][1,2,4]triazolo[4,3-a][1,4]diazepine 6-{4-[(4-trifluoromethylphenyl)thiomethyl]phenyl}-8,9-dihydro -1,4-dimethyl-4H,7H-cyclopenta[4,5]-thieno -[3,2-f][1,2,4]triazolo[4,3-a][1,4]diazepine (4S)-6-{2-chloro-4-[2-(4-trifluoromethylphenyl)ethyl]-phenyl}-8,9-dihydro-1,4-dimethyl-4H,7H-cyclopenta[4,5]-thieno[3,2-f][1,2,4]triazolo[4,3-a][1,4]diazepine (4S) thylphenyl)ethyl]phenyl}-8,9-dihydro -1,4-dimethyl-4H,7H-cyclopenta[4,5]thieno[3,2-f]-[1,2,4]triazolo[4,3-a][1,4]diazepine (4S)-6-[2-chloro-4-(2-phenylethyl)phenyl]-8,9-dihydro-1,4-dimethyl-4H,7H-cyclopenta[4,5]thieno[3,2-f][1,2,4]-triazolo[4,3-a][1,4]diazepine (4S)-6-[4-(2-phenylethyl)phenyl]-8,9-dihydro-1,4-dimethyl-4H,7H -cyclopenta[4,5]thieno[3,2-f][1,2,4]-triazolo[4,3-a][1,4]diazepine (4S)-6-{2-chloro-4-[2-(4-chlorophenyl)ethyl]phenyl}-8,9-dihydro -1,4-dimethyl-4H,7H-cyclopenta[4,5]-thieno[3,2-f]-[1,2,4]triazolo[4,3-a][1,4]diazepine (4S)-6-{4-[2-(4-chlorophenyl)ethyl]phenyl}-8,9-dihydro-1,4-dimethyl-4H,7H-cyclopenta[4,5]thieno[3,2-f][1,2,4]-triazolo[4,3-a][1,4]diazepine (4S)-6-{2-chloro-4-[(4-trifluoromethylphenyl)-thiomethyl]phenyl}-8,9-dihydro-1,4-dimethyl-4H,7H -cyclopenta[4,5]thieno[3,2-f][1,2,4]triazolo[4,3-a]-[1,4]diazepine (4S)-6-[4-[trifluoromethylphenyl)thiomethyl]phenyl]-8,9-dihydro -1,4-dimethyl-4H,7H-cyclopenta[4,5]-thieno[3,2-f]-[1,2,4]triazolo[4,3-a][1,4]diazepine

Galenic Preparations

EXAMPLE A

Tablets containing 10 mg of Substance B

Composition:

| | |
|---|---|
| Substance | 10.0 mg |
| Corn starch | 57.0 mg |
| Lactose | 48.0 mg |
| Polyvinylpyrrolidone | 4.0 mg |
| Magnesium stearate | 1.0 mg |
| | 120.0 mg |

Method of Preparation

The active substance, corn starch, lactose and polyvinylpyrrolidone are mixed together and moistened with water. The moist mixture is pressed through a 1.5 mm mesh screen and dried at about 45° C. The dry granules are pressed through a 1.0 mm mesh screen and mixed with magnesium stearate. The finished mixture is pressed in a tablet press using 7 mm diameter dies fitted with a dividing notch to form tablets. Weight of tablet: 120 mg Substance B = 6-(2-chloro-4-ethylphenyl-(4-trifluoromethylphenyl))-8,9-dihydro-1-methyl-4H,7H-cyclopenta -[4,5]thieno[3,2-f][1,2,4]triazolo[4,3-a][1,4]diazepine

EXAMPLE B

Coated tablets containing 5 mg of Substance B

Composition:

| | |
|---|---|
| Substance B | 5.0 mg |
| Corn starch | 41.5 mg |
| Lactose | 30.0 mg |
| Polyvinylpyrrolidone | 3.0 mg |
| Magnesium stearate | 0.5 mg |
| | 80.0 mg |

Method of Preparation

The active substance, corn starch, lactose and polyvinylpyrrolidone are thoroughly mixed and moistened with water. The moist mass is pressed through a 1 mm mesh screen, dried at about 45° C. and the granules are then passed through the same screen. After the addition of magnesium stearate, convex tablet cores with a diameter of 6 mm are made by compression in a tablet-making machine. The tablet cores thus produced are covered in known manner with a coating consisting essentially of sugar and talc. The finished coated tablets are polished with wax. Weight of coated tablet: 130 mg

EXAMPLE C

Tablets containing 50 mg of Substance B

Composition:

| | |
|---|---|
| Substance B | 50.0 mg |
| Calcium phosphate | 70.0 mg |
| Lactose | 40.0 mg |
| Corn starch | 35.0 mg |
| Polyvinylpyrrolidone | 3.5 mg |
| Magnesium stearate | 1.5 mg |
| | 200.0 mg |

Preparation

Substance B, calcium phosphate, lactose and corn starch are uniformly moistened with an aqueous polyvinylpyrrolidone solution. The mass is passed through a 2 mm mesh screen, dried at 50° C. in a circulating air dryer and screened again. After the lubricant has been added the granules are compressed in a tablet making machine.

EXAMPLE D

Capsules containing 50 mg of Substance B

Composition:

| | |
|---|---|
| Substance B | 50.0 mg |
| Corn starch | 268.5 mg |
| Magnesium stearate | 1.5 mg |
| | 320.0 mg |

Preparation

Substance B and corn starch are mixed together and moistened with water. The moist mass is screened and dried. The dry granules are screened and mixed with magnesium stearate. The finished mixture is packed into size 1 hard gelatine capsules.

EXAMPLE E

Suppositories containing 50 mg of Substance B

Composition:

| | |
|---|---|
| Substance B | 50 mg |
| Solid fat | 1,650 mg |
| | 1,700 mg |

Preparation

The hard fat is melted. At 40° C. the ground active substance is homogeneously dispersed. It is cooled to 38° C. and poured into slightly chilled suppository moulds.

EXAMPLE F

Oral suspension containing 50 mg of Substance B per 5 ml

Composition:

| | |
|---|---|
| Substance B | 50 mg |
| Hydroxyethylcellulose | 50 mg |
| Sorbic acid | 5 mg |
| 70% Sorbitol | 600 mg |
| Glycerol | 200 mg |
| Flavouring | 15 mg |
| Water to | 5 ml |

Distilled water is heated to 70° C. Hydroxyethyl-cellulose is dissolved therein with stirring. After the addition of sorbitol solution and glycerol it is cooled to ambient temperature. At ambient temperature, the sorbic acid, flavouring and Substance B are added. The suspension is evacuated with stirring to eliminate air.

Obviously, the other PAF-antagonists according to the invention may also be incorporated in the conventional galenic preparations in suitable doses.

An effective dose of the compounds according to the invention is between 1 and 100, preferably between 3 and 50 mg per dose, for oral use, between 0.001 and 50, preferably between 0.1 and 20 mg per dose for intravenous or intramuscular use. For inhalation it is advisable to use solutions containing 0.01 to 1.0, preferably 0.1 to 1% active substance.

EXAMPLE 4

[$^3$H]PAF receptor binding to vital human blood platelets

This experiment determined the competitive interaction of the test substances (in this case PAF-antagonists) with the known interaction of the radioligand [$^3$H]PAF to the same receptor.

The bonding studies were carried out on vital human thrombocytes. Blood samples from healthy donors were diluted with ACD buffer and centrifuged (15 minutes, 160×g). The platelet-rich plasma was purified by chromatography on Sepharose CL-2B (for eluting: HEPES buffer, pH 7.4, 20° C.).

Defined quantities (e.g., 800 µl) of the platelet suspension were incubated for 90 minutes at ambient temperature with:

a) a 30 pmolar [$^3$H]PAF solution diluted with buffer;
b) a 30 pmolar [$^3$H]PAF solution which simultaneously contains a µmolar (non-labelled) PAF solution; and
c) a 30 pmolar [$^3$H]PAF solution and the solutions of the test substances (different concentrations).

Incubation a) was used to determine total binding. Incubation b) was used to determine non-specific binding.

The reaction was stopped by vacuum filtering. The filters with the blood platelets were mixed with scintillation liquid and the residual radioactivity was measured in a counter. The specific binding was obtained from the total binding minus the non-specific binding. IC$_{50}$ values for each test substance were determined (the concentration of test substance which displaces 50% of the radioligand [$^3$H]PAF from the receptor) and K$_i$ values for each test substance were calculated therefrom. IC$_{50}$ and K$_i$ values are a measurement of the receptor affinity of the test substance. The lower the value of the IC$_{50}$ or K$_i$, the higher the affinity.

Results

| Test Substance | Binding K$_i$ [nMol/l] |
| --- | --- |
| Compound 1: | |
| 6-(4-(2-(4-trifluoromethylphenyl)ethyl)phenyl-8,9-dihydro-1-methyl-R,S-4-methyl-4H,7H-cyclopenta[4,5]thieno-[3,2-f][1,2,4]-triazolo[4,3-a][1,4]diazepine (Example 3) (racemate) | 0.79 |
| Compound 2: | |
| 6-(4-(2-(4-trifluoromethylphenyl)ethyl)phenyl-8,9-dihydro-1-methyl-S-4-methyl-4H,7H-cyclopenta[4,5]thieno-[3,2-f][1,2,4]-triazolo[4,3-a][1,4]diazepine (Example 3) (S-configuration) | 0.47 |

What is claimed is:

1. A diazepine of the formula:

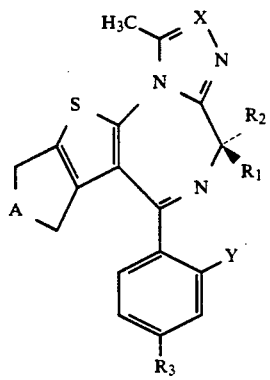

wherein

A represents —Ch$_2$— or —CH$_2$—CH$_2$—

X represents nitrogen, C—H or C—CH$_3$;

Y represents hydrogen or halogen;

R$_1$ represents hydrogen or CH$_3$;

R$_2$ represents hydrogen or CH$_3$;

R$_3$ represents

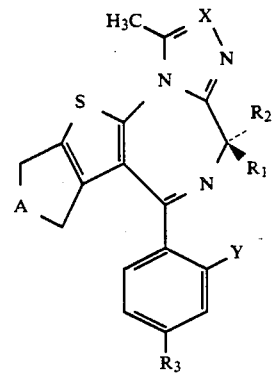

wherein n=1, 2, 3 or 4—preferably 2—, m=1, 2 or 3—preferably 1—,

R$_4$ represents hydrogen, halogen, CF$_3$, C$_{1-4}$-alkyl, C$_3$-C$_6$ cycloalkyl, methoxy, trifluoromethoxy, CN, k=1, 2 or 3 whilst if k is >1 R$_4$ may be identical or different, with the proviso that if Y represents hydrogen, R$_1$ and R$_2$ cannot both together represent hydrogen; optionally in the form of their racemates, enantiomers, diastereomers and mixtures thereof.

2. A diazepine of the formula:

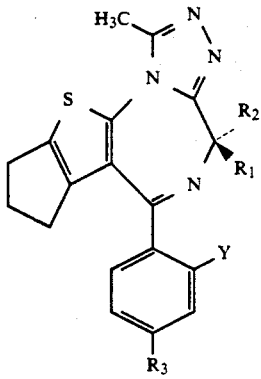

wherein

Y represents hydrogen, bromine or chlorine $R_1$ and $R_2$ are defined as hereinbefore;

$R_3$ represents

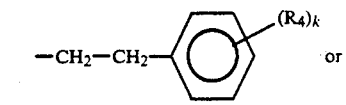 or

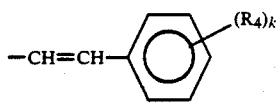

(in the trans configuration) or

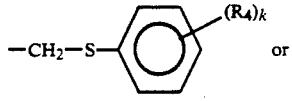 or

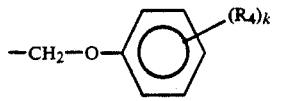

$R_4$ represents hydrogen, chlorine, bromine, trifluoromethyl, methyl, isobutyl or methoxy, whilst $R_4$ is preferably in the 4-position of the phenyl ring, optionally in the form of their racemates, enantiomers, diastereomers and mixtures thereof.

3. A diazepine as recited in claim 2, wherein the diazepine is S-configured, Y represents halogen, $R_1$ represents hydrogen and $R_2$ represents methyl.

* * * * *